United States Patent
Poland et al.

(10) Patent No.: US 6,824,514 B2
(45) Date of Patent: Nov. 30, 2004

(54) SYSTEM AND METHOD FOR VISUALIZING SCENE SHIFT IN ULTRASOUND SCAN SEQUENCE

(75) Inventors: McKee D. Poland, Andover, MA (US); Karl E. Thiele, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 16 days.

(21) Appl. No.: 10/270,278

(22) Filed: Oct. 11, 2002

(65) Prior Publication Data

US 2004/0073111 A1 Apr. 15, 2004

(51) Int. Cl.$^7$ ............................................... A61B 8/00
(52) U.S. Cl. ..................................................... 600/437
(58) Field of Search ............................. 600/437–472; 73/625, 626; 367/7, 11, 130, 138; 128/916

(56) References Cited

U.S. PATENT DOCUMENTS

| | | | |
|---|---|---|---|
| ,002,934 A | | 6/1843 | Oosawa |
| 5,181,513 A | | 1/1993 | Touboul et al. |
| 5,370,121 A | * | 12/1994 | Reichenberger et al. ..... 600/438 |
| 5,974,165 A | | 10/1999 | Giger et al. |
| 6,004,270 A | * | 12/1999 | Urbano et al. ............... 600/443 |
| 6,402,693 B1 | | 6/2002 | Emery ........................ 600/443 |

* cited by examiner

*Primary Examiner*—Ali Imam
(74) *Attorney, Agent, or Firm*—John Vodopia

(57) ABSTRACT

A system and method for visualizing scene shift over successive ultrasound scan frames is disclosed. In one embodiment the invention is a system for real-time visualization of scene shift in an ultrasound scan, comprising an ultrasound receiver for developing a first ultrasound image and a second ultrasound image, border formation software for determining a first border corresponding to the first ultrasound image and a second border corresponding to the second ultrasound image, and image misalignment detection software for overlaying the first border on the second border to determine whether the first border aligns with the second border. Corresponding systems, methods and computer-readable media are also disclosed.

33 Claims, 12 Drawing Sheets

SYSTEM AND METHOD FOR VISUALIZING SCENE SHIFT IN ULTRASOUND SCAN SEQUENCE

TECHNICAL FIELD

The present invention relates generally to ultrasonic diagnostic systems, and, more particularly, to a system and method for visualizing scene shift in an ultrasound scan sequence.

BACKGROUND OF THE INVENTION

Ultrasonic transducers and imaging systems have been available for quite some time and are particularly useful for non-invasive medical diagnostic imaging. Ultrasonic transducers are typically formed of either piezoelectric elements or of micro-machined ultrasonic transducer (MUT) elements. When used in transmit mode, the transducer elements are excited by an electrical pulse and in response, emit ultrasonic energy. When used in receive mode, acoustic energy impinging on the transducer elements is converted to a receive signal and delivered to processing circuitry associated with the transducer.

The transducer is typically connected to an ultrasound imaging system that includes processing electronics, one or more input devices and a suitable display on which the ultrasound image is viewed. The processing electronics typically include a transmit beamformer that is responsible for developing an appropriate transmit pulse for each transducer element, and a receive beamformer that is responsible for processing the receive signal received from each transducer element.

An ultrasonic transducer is typically combined with associated electronics in a housing. The assembly is typically referred to as an ultrasonic probe. Typically, ultrasonic probes are classified as either one-dimensional (1D) probes having a single element wide array of elements, or two-dimensional (2D) probes having a multiple element wide array. Furthermore, a probe referred to as a "bi-plane" probe includes two orthogonally positioned 1D arrays that may or may not intersect. A relatively new 2D probe, referred to as a "matrix probe" includes transducer elements arranged in two dimensions where each element is individually controllable, resulting in an ultrasound probe the scan lines of which can be electronically steered in two dimensions. Each dimension of a matrix probe can be thought of as a stack of contiguous linear arrays.

A matrix probe can comprise either a "fully sampled" or a "sparsely sampled" aperture. In a fully sampled aperture, every transducer element is individually addressable and controllable, and all elements are contiguous. In a sparsely sampled aperture, a subset of the physical set of transducer elements is addressed and controlled, or equivalently, there is a pattern of physical gaps between some elements such that they are not all contiguous. Sparsely sampled 2D arrays allow for fewer system connections (fewer channels) while still achieving distribution of the acoustic elements in two dimensions. However, a significant drawback of sparse 2D arrays is the loss of ability to control scan beam shape.

Regardless of the type of transducer probe, many medical ultrasound imaging techniques require that successive images, referred to as successive frames, of the same part of the anatomy be taken to view the selected piece of anatomy over a period of time. One examples of such a medical ultrasound imaging technique that develops successive ultrasound images over a period of time is the measurement of myocardial perfusion.

In a myocardial perfusion measurement, successive ultrasound scans of, for example, the left ventricle of a heart are triggered by the patient's electro-cardiogram (ECG) signal. One or more scans may be recorded per heartbeat, each at a specified delay from the ECG signal, so as to capture the same moment of the heartbeat cycle in a plurality of successive ultrasound scans, or frames. In such a measurement, the heart is imaged while an ultrasound contrast agent, such as a harmless solution of gas-filled microspheres, is introduced intravenously into the patient's blood stream. The contrast agent circulates through the patient and eventually into the heart.

Over a sequence of ECG triggered scan images, the volume of the contrast agent entering the myocardium is recorded by the resulting echo intensity in the sequence of ultrasound images. This sequence of images is used to analyze and measure the flow of myocardial perfusion from one image to the next.

One of the drawbacks of conventional ultrasound image processing systems is that the piece of the anatomy (i.e., the heart in a myocardial perfusion measurement) tends to move, over time, with respect to the transducer probe. This condition is referred to as "scene shift" over successive ultrasound images. Because the heart is in a different position during successive frames, the resulting sequence of images cannot be used to precisely determine the myocardial perfusion. This is so because, to facilitate automatic calculation of the change in intensity of the heart over time, it is necessary to align the ultrasound image data for each frame. In this manner, filtering and subtraction algorithms, for example, may operate without the detrimental effect of scene shift, which would otherwise cause apparent changes of contrast agent intensity.

One manner of addressing scene shift is to require that the patient hold their breath during successive ultrasound frames. Another manner of addressing this is for the ultrasound operator to be highly skilled in the placement and control of the ultrasound probe during successive frames. Unfortunately, both of these solutions leave much to be desired, as repeatable results are difficult to obtain.

Another manner of addressing scene shift is to employ an image alignment algorithm. Unfortunately, an image alignment algorithm is costly to implement and consumes valuable processing resources.

Another example of a medical ultrasound imaging technique that develops successive ultrasound images over a period of time is three dimensional (3D) ultrasound imaging. Modern 3D-ultrasound imaging systems generate planar scans at varying angles to the face of the transducer probe. The scan planes, referred to as slices, comprising a number of individual scan lines, are used to interrogate a volume. 3D imaging is also useful for collecting successive images, but is resource inefficient in that a large number of scan planes must be collected to interrogate a volume.

The frame size in 3D imaging is typically limited by the amount of time consumed in generating and collecting ultrasound echoes from each scan lime. The total time is referred to as "frame time." The reciprocal of frame time is "frame rate." The frame rate should generally be above 15 Hz for most cardiac scanning applications. Unfortunately, a 15 Hz frame rate limits the size of the volume that can be scanned, thereby making it difficult to image the entire heart.

One solution to this acoustic limitation is to collect "sub-volume" scans over multiple heartbeats. Each of the sub-volume scans can be triggered by the above-mentioned ECG signal, and can be taken at an optimal frame rate, but is positioned at a sequential angle such that the edges of the sub-volume scans are adjacent. An image processing system associated with the ultrasound imaging system concatenates the sub-volume scans into a larger, complete volume scan.

Unfortunately, this scanning methodology also suffers from the detrimental effects of scene shift. The relative positions of the sub-volumes must be true to the positions assumed when the ultrasound energy is shifted to the sequential angles for each successive sub-volume scan. To compensate for this, as mentioned above, the patient is frequently asked to hold their breath during successive scans.

Therefore, it would be desirable to have an ultrasound imaging system capable of visualizing scene shift and determining whether the imaging subject has been displaced from one image to the next.

SUMMARY

Embodiments of the invention include a system and method for visualizing scene shift in an ultrasound scan. In one embodiment the invention is a system for real-time visualization of scene shift in an ultrasound scan, comprising an ultrasound receiver for developing a first ultrasound image and a second ultrasound image, border formation software for determining a first border corresponding to the first ultrasound image and a second border corresponding to the second ultrasound image, and image misalignment detection software for overlaying the first border on the second border to determine whether the first border aligns with the second border.

Other systems, methods, computer readable media, features, and advantages of the invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention, as defined in the claims, can be better understood with reference to the following drawings. The components within the drawings are not necessarily to scale relative to each other, emphasis instead being placed upon clearly illustrating the principles of the present invention.

DETAILED DESCRIPTION OF THE PREFERRED EMBODIMENT

Figure 1:
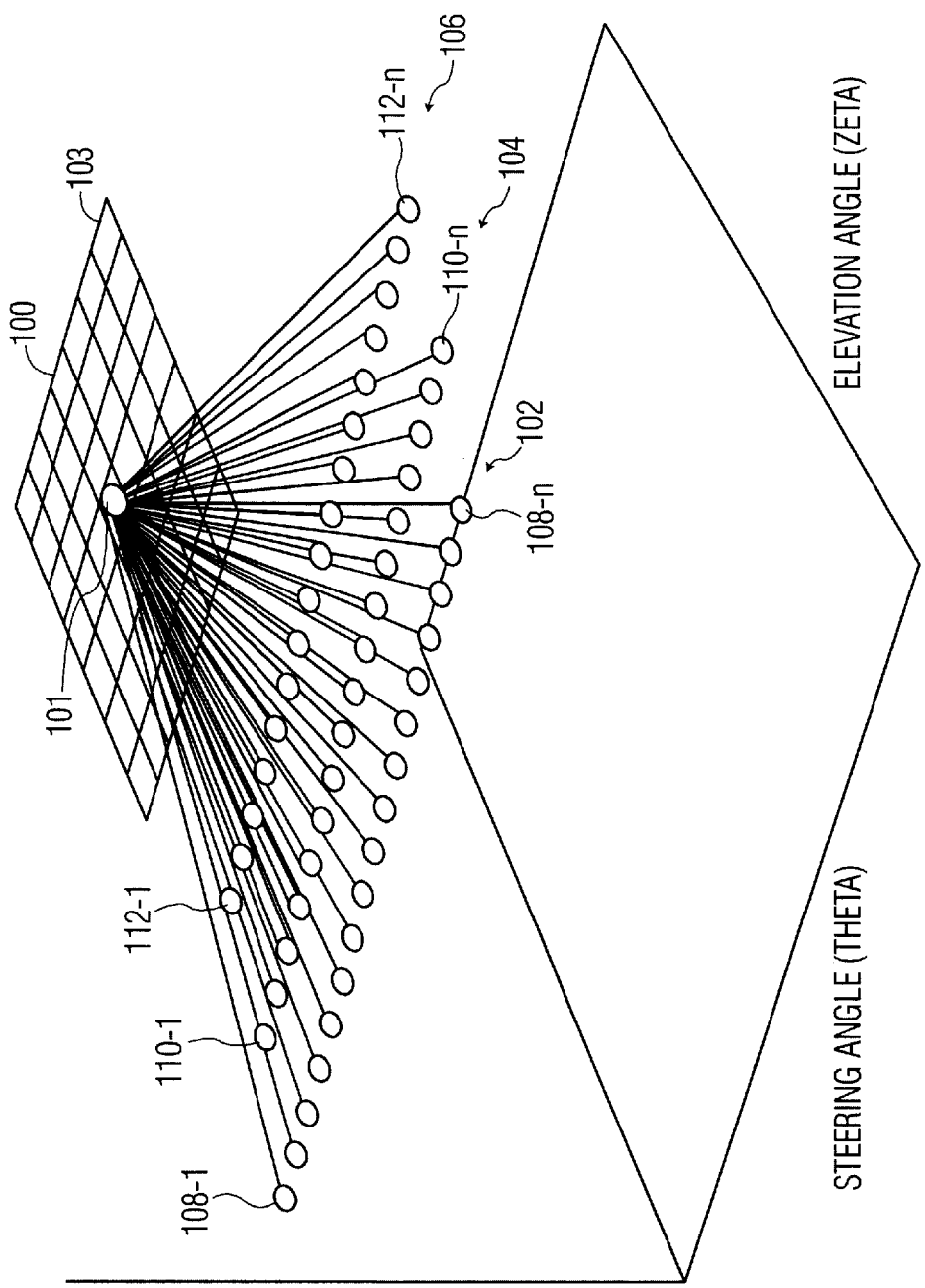
FIG. 1 is a schematic diagram illustrating the manner in which an ultrasound probe develops scan slices and uses the scan slices to interrogate a volume.

The invention described hereafter is applicable to any ultrasound imaging system in which it is desirable to capture a sequence of ultrasound images over a period of time. Furthermore, the following description is presented in terms of routines and symbolic representations of data bits within a memory associated processors and possible networks or networked devices. These descriptions and representations are used by those having ordinary skill in the art to effectively convey the substance of their work to others having ordinary skill in the art. A routine embodied in software is here, and generally, intended to be a self-consistent sequence of steps or actions leading to a desired result. Thus, the term "routine" is generally used to refer to a series of operations stored in a memory and executed by a processor. The processor can be a central processor of an ultrasound imaging system or can be a secondary processor of the ultrasound imaging system. The term "routine" also encompasses such terms as "program," "objects," "functions," "subroutines," and "procedures."

In general, the sequence of steps in the routines requires physical manipulation of physical quantities. Usually, though not necessarily, these quantities take the form of electrical or magnetic signals capable of being stored, transferred, combined, compared or otherwise manipulated. Those having ordinary skill in the art refer to these signals as "bits," "values," "elements," "characters," "images," "terms," "numbers," or the like. It should be understood that these and similar terms are to be associated with the appropriate physical quantities and are merely convenient labels applied to these quantities.

In the present application, the routines, software, and operations are machine operations performed in conjunction with human operators. In general, the invention relates to method steps, software and associated hardware including a computer readable medium configured to store and execute electrical or other physical signals to generate other desired physical signals.

The apparatus of the invention is preferably constructed for the purpose of ultrasonic imaging. However, a general-purpose computer can perform the methods of the invention or other networked device selectively activated or reconfigured by a routine stored in the computer and coupled to ultrasound imaging equipment. The procedures presented herein are not inherently related to any particular ultrasonic imaging system, computer or apparatus. In particular, various machines may be used with routines in accordance with the teachings of the invention, or it may prove more convenient to construct more specialized apparatus to perform the method steps. In certain circumstances, when it is desirable that a piece of hardware possess certain characteristics, these characteristics are described more fully below.

With respect to the software routines described below, those having ordinary skill in the art will recognize that there are a variety of platforms and languages for creating instruction sets for performing the routines described below. Those having ordinary skill in the art will also recognize that the choice of the exact platform and language is often dictated by the specifics of the actual system constructed, such that what may work for one type of system may not be efficient on another system.

FIG. 1 is a schematic diagram illustrating the manner in which an ultrasound probe develops scan slices and uses the scan slices to interrogate a volume. Ultrasound data is typically acquired in frames, where each frame represents one or more sweeps of an ultrasound beam emanating from the face of the probe 100. The probe 100 includes a two-dimensional array of transducer elements; an exemplar one of which is illustrated using reference numeral 103. Such a sweep is typically developed by generating a large number of individual scan lines along one scan plane. An example of one scan plane, or "slice," is illustrated using reference numeral 102 and the scan plane comprises individual scan lines 108-1 through 108-n. In this case, each slice is in the shape of a sector, and the "origin" 101 of each scan line is located at the center of the surface of the physical face of the probe 100.

The scan lines are typically steered in 2 dimensions during scan sweeps to create a set of rastered scan slices, exemplar ones of which are illustrated as slices 102, 104 and 106, where each slice interrogates a 2-dimensional "sector region" of the field of view. In effect, each slice 102, 104 and 106 represents a traditional two-dimensional sweep, with each sweep being displaced in elevation from the neighboring sweep. Those having ordinary skill in the art will recognize that trapezoidal or parallelogram shapes can be generated for each of the slices instead of sectors. Furthermore, a large number of such slices, slightly displaced in elevation, can be used to interrogate a volume.

Assembling the data from the sector slices produces a three-dimensional set of data referred to as a scan volume. Since all of the lines originate from the same point, the rendered 3D volume appears as a pyramid or cone, where the apex of the volume is the scan origin at the transducer probe face, which is located at the patient's skin surface.

An ultrasound imaging systems develops this volume scan by generating multiple slices in at least two dimensions. These multiple slices generate ultrasound data for the volume occupied by the slices. To produce three-dimensional images, this volume of data is then processed by the ultrasound imaging system to create an image for display on a two-dimensional surface (such as the surface of the CRT type display) that has the appearance of being three-dimensional. Such processing is typically referred to as a rendering.

Figure 2:
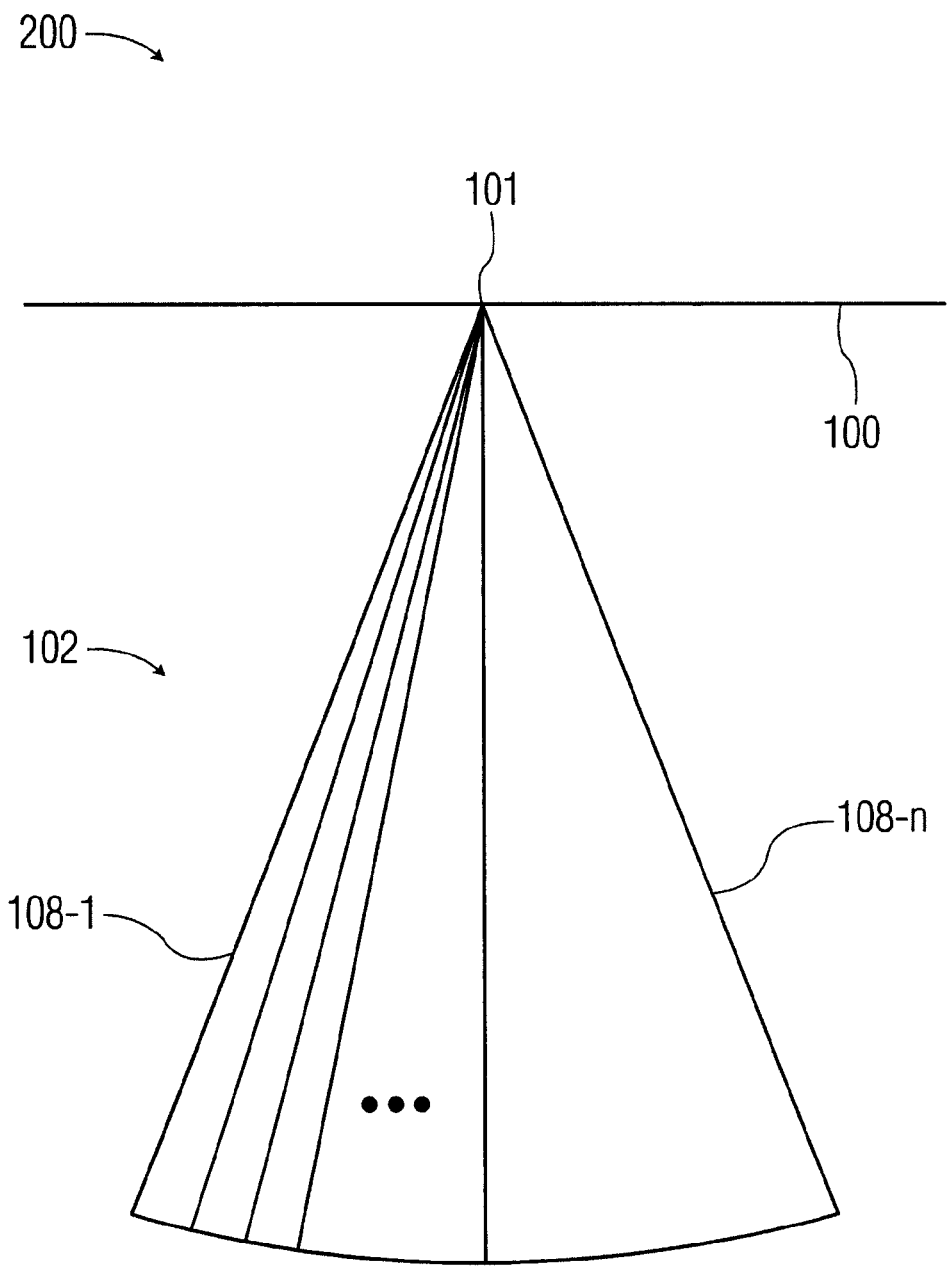
FIG. 2 is a graphical representation of one of the ultrasound slices of FIG. 1.

FIG. 2 is a graphical representation of one of the ultrasound slices of FIG. 1. The slice 102 includes scan lines 108-1 through 108-n emanating from the origin 101 of the transducer probe 100.

Figure 3:
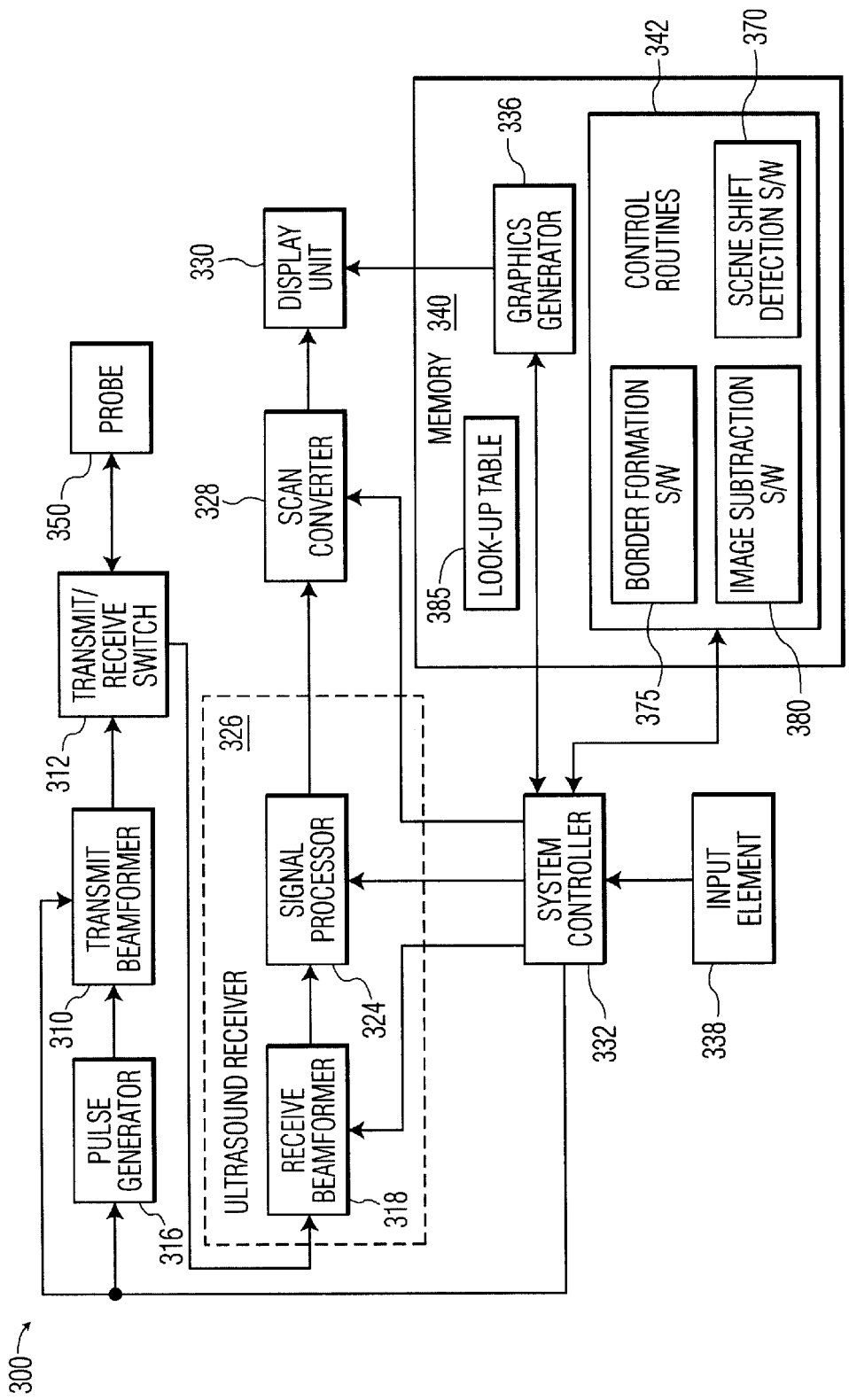
FIG. 3 is a block diagram illustrating an ultrasound imaging system in accordance with an embodiment of the invention.

FIG. 3 is a block diagram illustrating an ultrasound imaging system 300 in accordance with an embodiment of the invention. It will be understood by those having ordinary skill in the art that the ultrasound imaging system 300, as illustrated in FIG. 3, and the operation thereof as described below, is intended to be generally representative of such systems and that any particular system may differ significantly from that shown in FIG. 3. The ultrasound imaging system 300 includes a transmit beamformer 310 coupled through a transmit receive (T/R) switch 312 to a probe 350. While the probe 350 may be any transducer probe, a matrix transducer probe will be discussed for simplicity. The matrix probe 350 includes a matrix transducer array having a plurality of transducer elements arranged across two dimensions. The system 300 can randomly select any point on the matrix probe 350 as the point from which the ultrasonic energy is projected. While the matrix probe 350 will be referred to as a fully sampled array, a sparse array configuration is also possible. As described above, a fully sampled array is one in which each element is individually addressable. Either fully sampled or sparse array configurations may benefit from the various embodiments of the invention to be described below.

The T/R switch 312 typically includes one switch element for each transducer element. Alternatively, the matrix probe 350 may have multiplexing circuitry, or the like, to reduce the number of leads between the T/R switch 312 and the matrix probe 350, thereby reducing the number of required switches. The transmit beamformer 310 receives pulsed sequences from a pulse generator 316. The matrix probe 350, energized by the transmit beamformer 310, transmits ultrasound energy into a region of interest in a patient's body and receives reflected ultrasound energy, commonly referred to as echoes, from various structures and organs within the body. As is known by those having ordinary skill in the art, by appropriately delaying the waveforms applied to each transducer element by the transmit beamformer 310, a focused ultrasound beam may be transmitted from the matrix probe 350.

The matrix probe 350 is also coupled, through the T/R switch 312, to a receive beamformer 318. Ultrasound energy from a given point within the patient's body is received by the transducer elements at different times. The transducer elements convert the received ultrasound energy to transducer signals which may be amplified, individually delayed and then summed by the receive beamformer 318 to provide a beamformed signal that represents the received ultrasound levels along a desired receive line ("beam"). The receive beamformer 318 may be a digital beamformer including an analog-to-digital converter for converting the transducer signals to digital values, or may be an analog beamformer. As known to those having ordinary skill in the art, the delays applied to the transducer signals may be varied during reception of ultrasound energy to effect dynamic focusing. The process is repeated for multiple scan lines to create a frame of data for generating an image of the region of interest in the patient's body.

Even though known systems employing matrix probes concentrate on scanning complete volumes, the matrix probe 350 is capable of providing a variety of scan patterns such as a sector scan, where scan lines may appear to originate at any point on the matrix probe 350 and are directed at different angles, a linear scan, a curvilinear scan and other scan patterns.

The receive beamformed signals are then applied to a signal processor 324, which processes the beamformed signal to create a detected, filtered stream of digital data representing the strength of echoes along each scan line. The receive beamformer 318 and the signal processor 324 comprise an ultrasound receiver 326. The output of the signal processor 324 is supplied to a scan converter 328, which converts sector scan and other scan pattern signals to conventional raster scan display formats. The output of the scan converter 328 is supplied to a display unit 330, which displays an image of the region of interest in the patient's body.

The system controller 332 provides overall control of the system. The system controller 332 performs timing and control functions and typically includes a microprocessor operating under the control of graphics generator 336, control routines 342, and a look-up table (LUT) 385, all contained within memory 340. The control routines 342 also include scene shift detection software 370, which can also be referred to as image misalignment detection software, image border formation software 375, and image subtraction software 380. As will be described in further detail below, the control routines 342, scene shift detection software 370, image border formation software 375, image subtraction software 380 and the graphics generator 336, in cooperation with the system controller 332 enable the ultrasound imaging system 300 to process successive ultrasound image frames to determine whether scene shift has occurred in the successive image frames.

For example, in one exemplary embodiment, a border of a particular part of the anatomy that is being imaged can be generated for each of a plurality of successive ultrasound image frames. The border can be highlighted using, for example, a differentiating color, and then superimposed, or overlaid, over a successive image frame. By accumulating border information over multiple image frames, the ultrasound imaging system 300 can display the overlaid borders progressively through the sequence. In this manner a user of the ultrasound imaging system 300 can determine whether scene shift has occurred in the successive images.

Alternative methodologies for determining whether scene shift has occurred will be described below. For example, in an alternative embodiment, a first ultrasound image can be subtracted from a second ultrasound image to determine whether successive image frames have moved with respect to each other.

The system controller 332 also uses the memory 340 to store intermediate values, including system variables describing the operation of the ultrasound imaging system 300. Although not shown, an external storage device may be used for permanent and/or transportable storage of data. Examples of devices suitable for use as an external storage element include a floppy disk drive, a CD-ROM drive, a videotape unit, etc.

In accordance with an aspect of one embodiment of the invention, border information for successive ultrasound images is generated by the image border formation software 375. The border information is used by the scene shift detection software 370 to present the border information from a previous image frame on a successive image frame. In this manner, a user of the system 300 can determine whether the images align (i.e., no scene shift) or not (i.e., scene shift has occurred).

In accordance with an alternative embodiment of the invention, an ultrasound image is subtracted from a subsequent ultrasound image by the image subtraction software 380. The resultant image or portions thereof, is used by the scene shift detection software 370 to present an image to the user. The image, or portion of the image, can be used to determine whether the images align (i.e., no scene shift) or not (i.e., scene shift has occurred). It should be mentioned that an ultrasound system might not include both the border detection software 375 and the image subtraction software 380, depending on specific implementation details.

A user communicates commands to the ultrasound imaging system 300 via the input element 338, which may include, among other devices, a mouse, keyboard, stylus, or may include a combination of input devices, such as keys, sliders, switches, touch screens, a track ball, or other input devices that enable the user of the ultrasound imaging system 300 to communicate the desired position, shape, transmit/receive frequencies, amplification, etc. of the ultrasound image to the system controller 332. When the desired ultrasound image parameters are communicated to the system controller 332, the system controller 332, in cooperation with the control routines 342 and the graphics generator 336, determines the appropriate scan lines that should be projected by the matrix probe 350 to achieve the desired ultrasound image communicated to the system controller 332 via input element 338. The system controller 332 then communicates with the pulse generator 316 and the transmit beamformer 310 in order to generate such appropriate scan lines.

In an alternative system configuration, different transducer elements are used for transmitting and receiving. In such a configuration, the T/R switch 312 may not be required, and the transmit beamformer 310 and the receive beamformer 318 may be connected directly to the respective transmit and receive transducer elements.

Figure 4A:
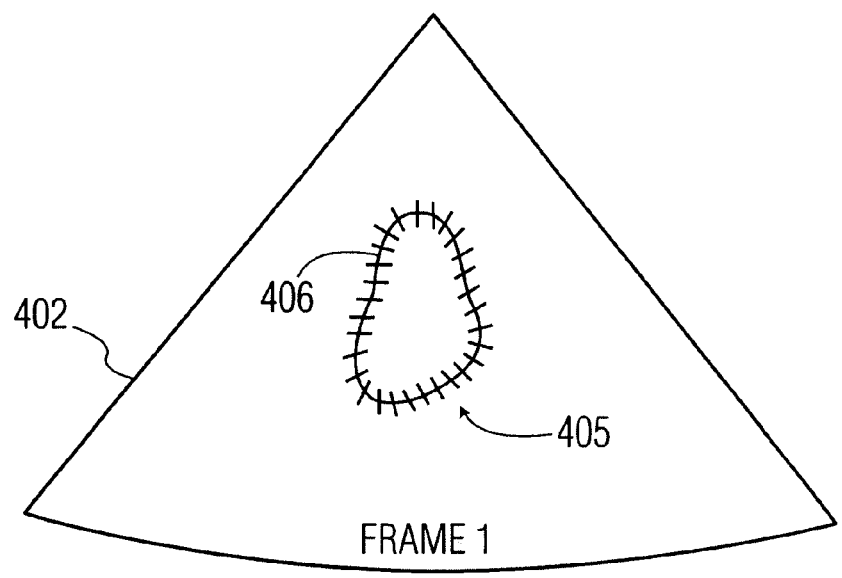
FIGS. 4A through 4D are a series of graphical illustrations depicting the operation of a first embodiment of the invention.

FIGS. 4A through 4D are a series of graphical illustrations depicting the operation of a first embodiment of the invention. In FIG. 4A, a scan slice 402, sometimes referred to as a frame, displays a first ultrasound image 405. The first ultrasound image 405 can be obtained and displayed using the ultrasound imaging system 300. In a medical ultrasound imaging application, the first ultrasound image 405 may be an ultrasound image of, for example, a human heart. When it is desirable to capture multiple sequential ultrasound images of a portion of anatomy, the first ultrasound image 405 may represent a depiction of a heart during a particular period of a heartbeat cycle. The first ultrasound image 405 may be triggered by, for example, an ECG signal.

In accordance with a first embodiment of the invention, the data that represents first ultrasound image 405 is stored in memory (e.g., 340 of FIG. 3) and is processed by the border formation software 375 (FIG. 3) so that an outline of the border, illustrated using reference numeral 406, of the first ultrasound image 405 is generated. The border formation is preferably done by processing individual acoustic lines. The border formation software 375 detects regions in acoustic lines where the echoes rapidly change in intensity over a short line distance, indicating the change in echo intensity across a tissue border. The input to the border formation software 375 is beamformed, detected acoustic scan line data as a series of samples. The output of the border formation software 375 is an equivalently sized set of border samples, comprising low (non-border) values over regions that vary slowly in acoustic echo intensity along the scan line, and high (border) values over regions of rapidly varying intensity along the scan line. To obtain the border values, samples are first passed through a low-pass finite impulse response (FIR) filter, and then differentiated using the nth difference (the numerical difference between the current sample and the nth previous sample). The output samples of the difference step are each compared to a pre-determined threshold, which may be adjusted by the user to control the sensitivity of the border detection. The numerical amount, or value, by which the sample exceeds the border threshold is mapped to a final border signal value through a look-up table (LUT) 385 located in the memory 340.

The content of the LUT is configurable to adjust the behavior of the border formation software 375, but a simple, monotonic input function may be used, which produces high value border samples for medium to high input values and low or 0 value border samples for low input values. The border signal samples are scan converted in the scan converter 328 and displayed like the image data, preferably overlaying the border in a different display color. Where the border signal samples are low, there is no overlay and the image data shows. Where the border signal samples are high, the border colors override the image data. The formation of the outline of the border is shown in FIG. 4A using the outline of the border 406 formed from the first ultrasound image 405.

Figure 4B:
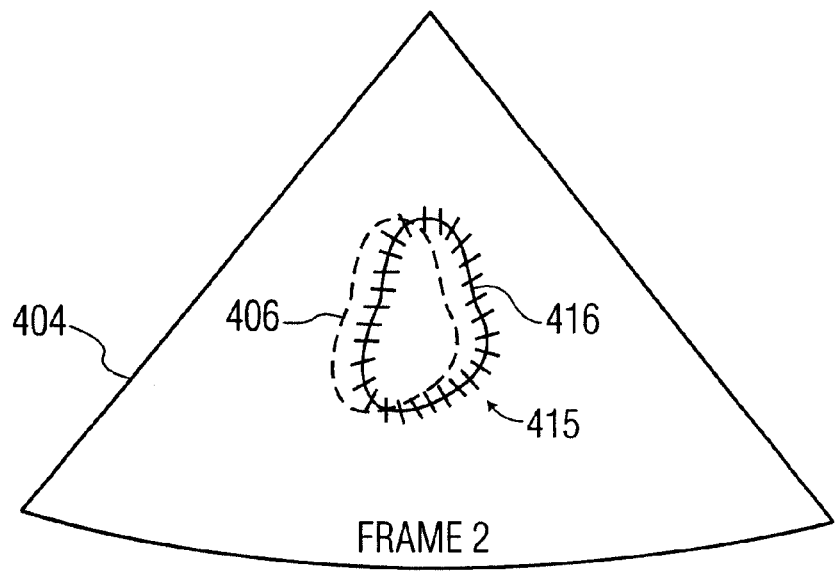

As illustrated in FIG. 4B, and in accordance with this embodiment of the invention, a subsequent (second) ultrasound image 415 is obtained by the ultrasound imaging system 300 and displayed in the scan slice 404. To determine whether the subject in the scan slice 404 is in the same relative position as the subject in the scan slice 402 (i.e., to determine whether scene shift has occurred between the first ultrasound image 405 and the second ultrasound image 415), the border formation software 375 develops an outline 416 of the border of the second ultrasound image 415. The scene shift detection software 370 (FIG. 3) overlays the outline 416 of the second ultrasound image 415 over the border 406, illustrated using a dotted line, of the first ultrasound image 405 in scan slice 404.

For example, to easily distinguish the outline 406 from the outline 416 of the second ultrasound image 415, the outline 406 may be presented in a different color from the color of the second ultrasound image 415. In this manner, a user viewing the display 330 (FIG. 1) can easily determine whether scene shift has occurred between the first ultrasound image 405 and the second ultrasound image 415. In the example shown in FIGS. 4A and 4B, scene shift has occurred because, as shown in FIG. 4B, the outline 406 of the first ultrasound image 405 is shown spatially displaced from the outline 416 of the second ultrasound image 415. In this manner, a user of the ultrasound system 300 can determine immediately whether to perform the ultrasound scan again, rather than discovering upon later review that the images were unsuitable for post-processing, after the patient has departed.

Figure 4C:
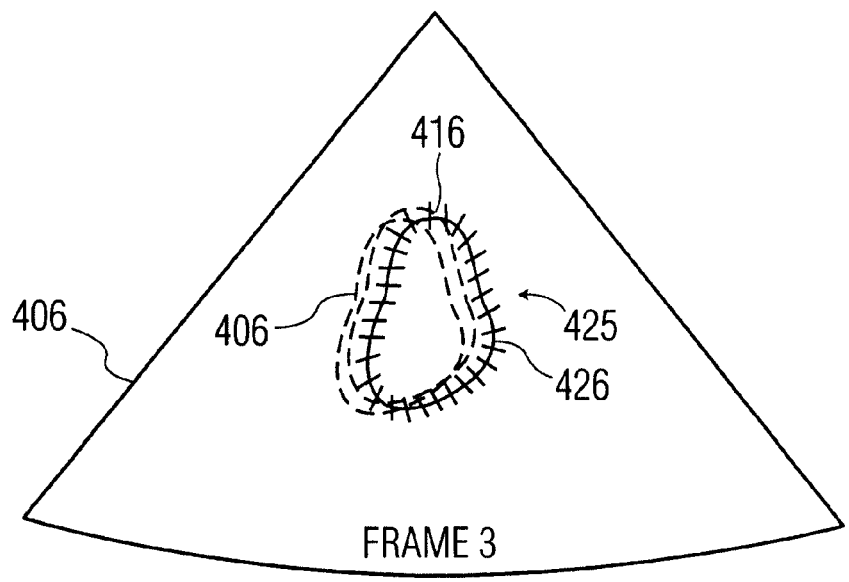
Figure 4D:
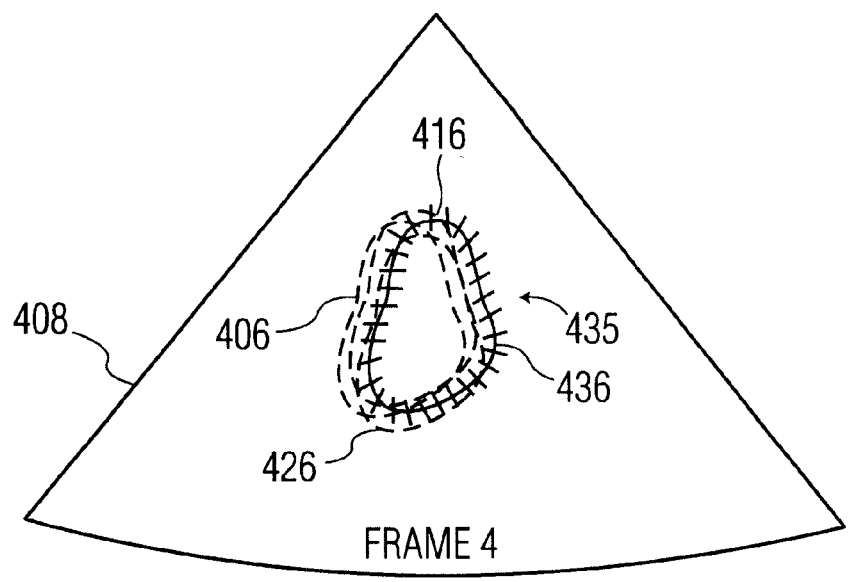

FIG. 4C is a graphical illustration depicting another subsequent (third) ultrasound scan. The scan slice 406 includes the outline 406 of the first ultrasound image 405 and includes an outline 416 of the second ultrasound image 415. In accordance with this aspect of the invention, the scan slice 406 includes a third ultrasound image 425 and its outline 426, over which the outline 406 and the outline 416 are overlaid. This process can be performed for many successive ultrasound scan frames, culminating in an image such as the one shown in FIG. 4D. In FIG. 4D, the outline 406 of the first ultrasound image 405, the outline 416 of the second ultrasound image 415, and the outline 426 of the third ultrasound image 425 are overlaid on a fourth ultrasound image 435 and its respective outline 436, which are all presented in the scan frame 408. In this manner, a user of the system can simultaneously view the positions of many subsequent ultrasound images to determine whether the ultrasound subject anatomy (in this example, the human heart) has moved from one image frame to another.

In an alternative implementation, an outline of a portion of anatomy can be generated and stored for multiple sequential scan frames, forming a dynamic reference image, which may then be selectively overlaid on subsequent images. The dynamic reference image could, for example, be any of the images in FIGS. 4A through 4D and could vary over the cardiac cycle, resulting in a sequence of reference images, any of which may be chosen for comparison with the corresponding image from a subsequent cardiac cycle. These multiple reference images could be operated on by the border formation software 375, which develops an outline (i.e., the border image) of each reference image as described above.

The dynamic reference images could be captured and generated during a reference cardiac cycle. The ultrasound imaging system 300 could capture subsequent images, triggering, for example, on the ECG signal, and form border images for those as described above. The system 300 would then select and overlay the appropriate reference border image over the subsequent "live" border image, thus allowing the operator of the ultrasound imaging system 300 to accurately position the probe in real time throughout multiple cardiac cycles. To match a reference image border with the corresponding "live" image border, the system 300 preferably selects the reference image based on the time elapsed since the last ECG trigger, or alternatively, by counting the same number of reference image scan frames since the ECG trigger as the currently displayed image.

Another alternative is to allow the user to select which of the dynamic reference border images to overlay. That is, which frames of the cardiac cycle on which to compare borders, so that only selected portions of the cycle are used for verifying alignment, and the others are imaged without the overlay. This would allow the user to maximize the diagnostic utility of the images captured while still using one or more for verifying alignment.

Figure 5A:
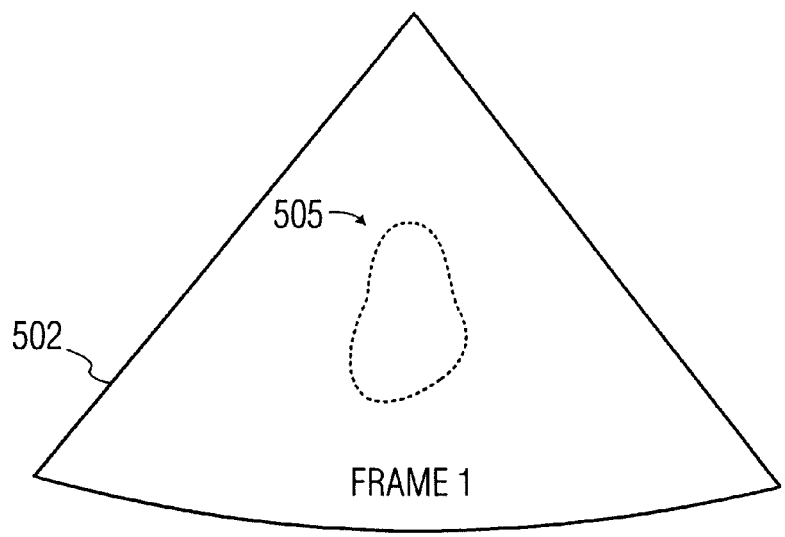
FIGS. 5A through 5H are a series of graphical illustrations depicting a second embodiment of the invention.
Figure 5B:
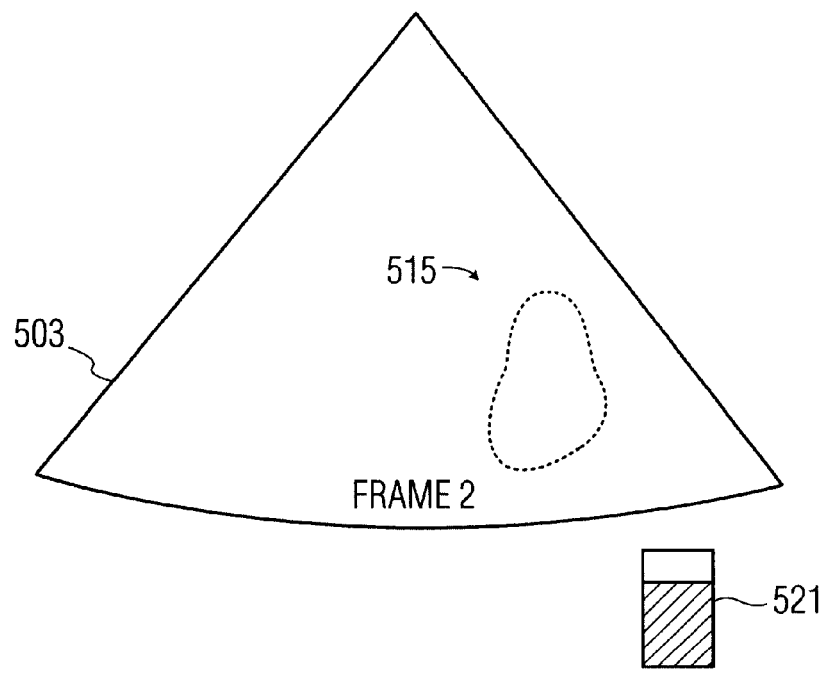

FIGS. 5A through 5G are a series of graphical illustrations depicting a second embodiment of the invention. In FIG. 5A, a scan slice 502 illustrates a first ultrasound image 505. The first ultrasound image 505 is similar to the first ultrasound image 405 described above. FIG. 5B depicts a subsequent ultrasound scan slice 503 having a subsequent ultrasound image 515. The subsequent ultrasound image 515 is displayed to the user in the normal fashion.

Figure 5C:
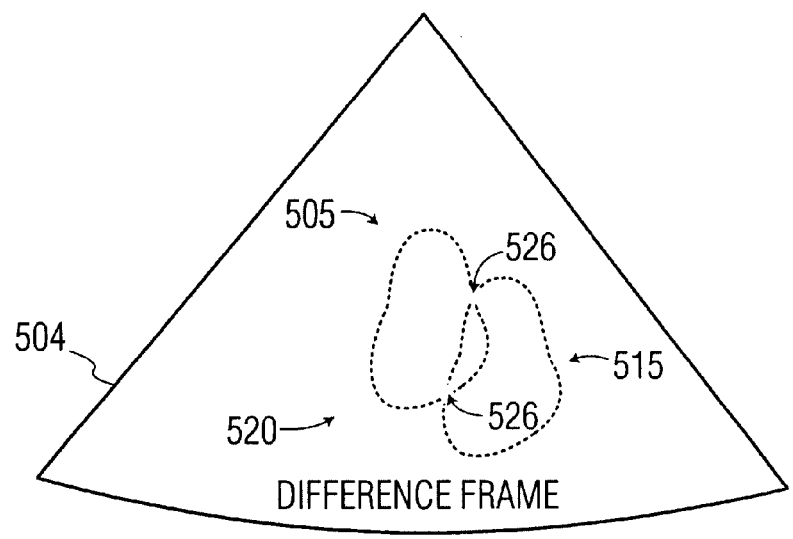

In FIG. 5C, the first ultrasound image 505 is depicted in scan slice 504 along with the subsequent ultrasound image 515. However, in this embodiment, to determine whether scene shift has occurred, the image subtraction software 380 (FIG. 1) mathematically operates on the data that represents the first and second ultrasound images 505 and 515. Specifically, the image subtraction software 380 (FIG. 1) subtracts the first ultrasound image 505 from the subsequent ultrasound image 515, and generates a resultant image, sometimes referred to as a "difference" image, or a "difference" frame. The difference image is depicted as image 520 in FIG. 5C. In this example, image 515 is shifted down and to the right with respect to image 505. In FIG. 5C, it is shown that in the overlap regions 526 where the two images overlap, the difference image 520 is minimal, producing patches 526 of absence in the image 520 where the images 505 and 515 overlap. The areas where the images do not overlap are indicative of scene shift between the two images 505 and 515. In these areas, the difference image 520 is relatively intense.

The scan slice 504 is preferably not displayed to the user. Rather it is generated internal to the memory of image subtraction software 380. However, the scan slice 504 and the difference image 520 are depicted in FIG. 5C for ease of illustration. The image subtraction software 380 further calculates the average intensity of the difference image 520 and uses the average intensity to generate a numeric or graphic indication of scene shift, preferably in the form of a bar graph 521, as shown in FIG. 5B. Because there is significant scene shift between the first ultrasound image 505 and the subsequent ultrasound image 515, the graphic indicator 521 is relatively high. Other forms of graphic indicator can also be used.

Figure 5D:
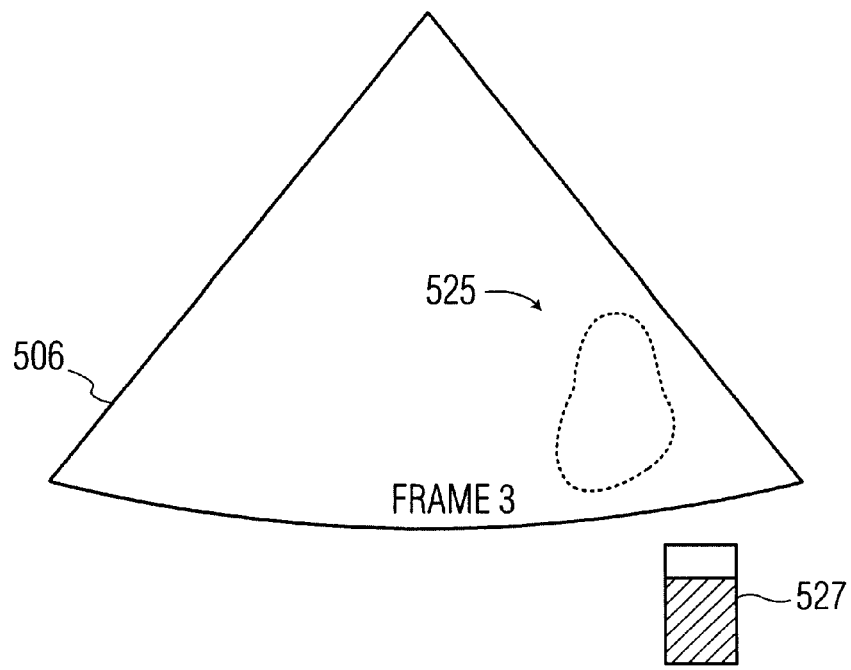
Figure 5E:
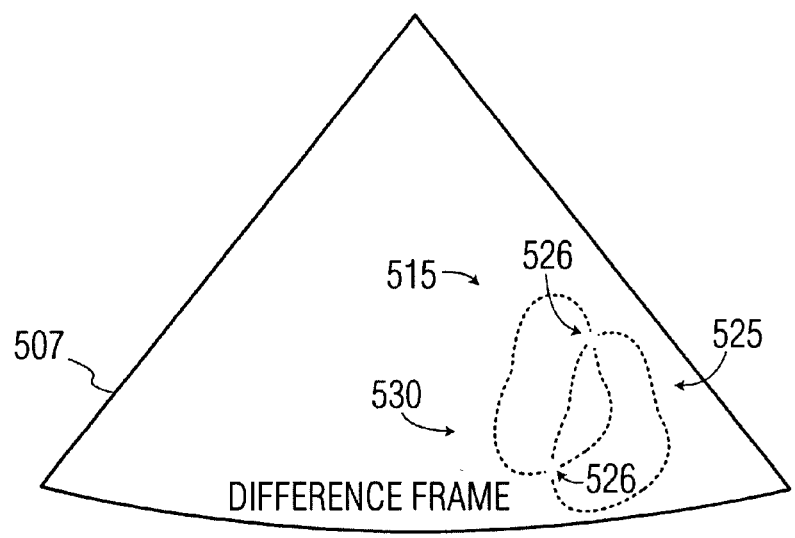

FIG. 5D shows a scan slice 506 having another subsequent ultrasound image 525. The subsequent ultrasound image 525 is in a different relative position in the scan slice 506 than the previous ultrasound image 515 in scan slice 503. FIG. 5E illustrates the difference image 530. In FIG. 5E, it is shown that in the regions where the two images 515 and 525 overlap, the difference image 530 is minimal, producing patches 526 of absence in the image 530 where the ultrasound images 515 and 525 overlap. The areas where the images 515 and 525 do not overlap are indicative of scene shift between the two images 515 and 525. In these areas, the difference image 530 is relatively intense.

As mentioned above with respect to scan slice 504, the scan slice 507 preferably is not displayed to the user. Rather it is generated internal to the memory of image subtraction software 380. The image subtraction software 380 further calculates the average intensity of the difference image 530 and uses the average intensity to generate a numeric or graphic indication of scene shift. As illustrated above, the graphic indicator 527 in FIG. 5D indicates a relatively high degree of scene shift between the images 515 and 525.

Figure 5F:
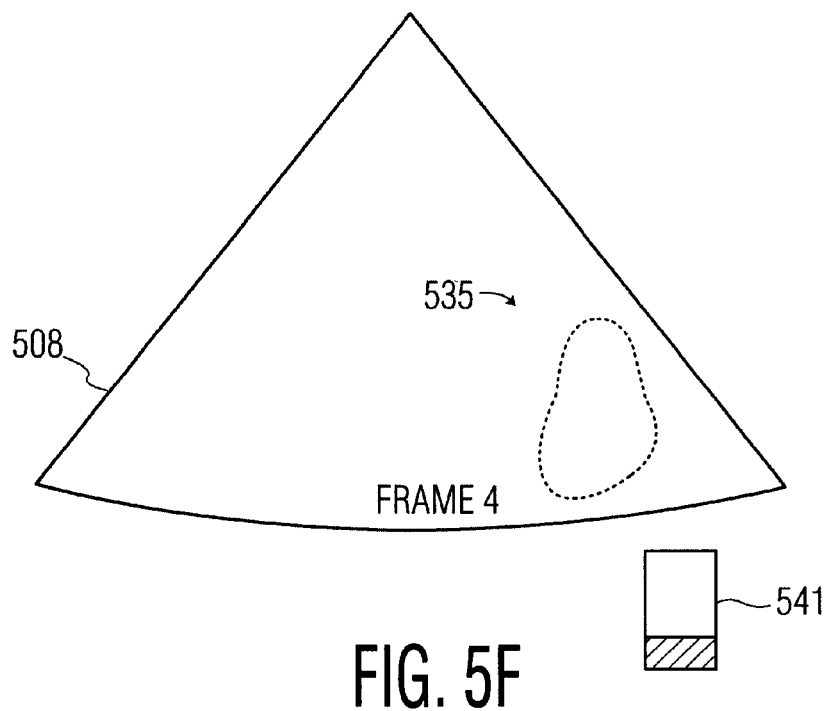
Figure 5G:
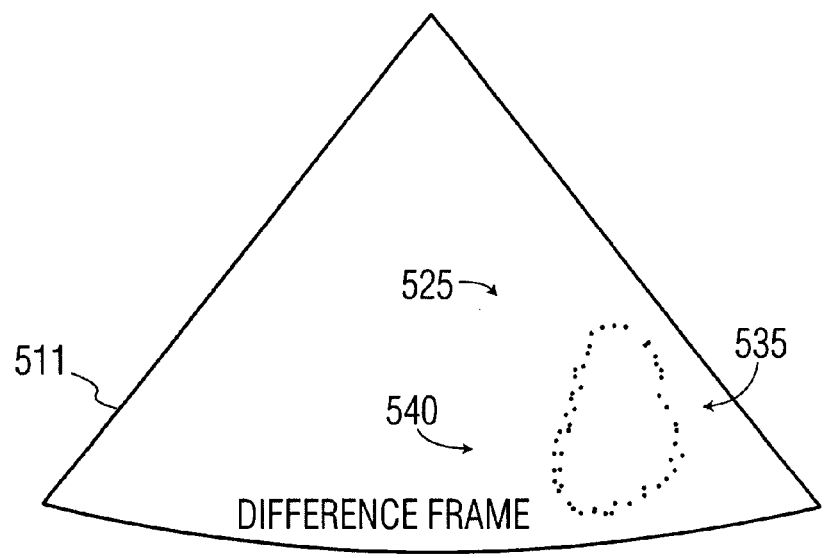

FIG. 5F shows a scan slice 508 having another subsequent ultrasound image 535. However, the subsequent ultrasound image 535 is substantially in the same relative position as the ultrasound image 525 of FIG. 5D. FIG. 5G illustrates the difference image 540. In FIG. 5G, because the image 535 is in substantially the same relative position as the image 525, a small degree of scene shift has occurred. Accordingly, there is predominately a large area in which the two images 525 and 535 overlap, resulting in a small difference image 540. This result in a graphic indicator 541 displaying a relatively low indicator of scene shift in FIG. 5F.

As mentioned above with respect to scan slices 504 and 507, the scan slice 511 preferably is not displayed to the user. Rather it is generated internal to the memory of image subtraction software 380. In another alternative implementation, the system can be used for real-time visualization of relative probe position. In this regard, a first ultrasound reference image is captured. A graphical representation of the reference image is generated for display and a second ultrasound image is captured. The graphical representation of the reference image is overlaid on the second ultrasound image, thereby allowing the user to determine the real-time position of the ultrasound probe. To aid in probe placement, the reference image is displayed in a color different than a color of the second ultrasound image. Alternatively, other differentiating parameters can be used to distinguish the reference image from the second image. Further, the graphical representation of the reference image can be stored on the system for use as a reference for a second ultrasound scan acquired in a separate scan sequence from the one used to acquire the reference image.

The first ultrasound reference image may be displayed on the display unit 330 or may be stored internally in, for example, the memory 340. The graphical representation of the reference can be, as described above, the detected border 406 as shown in FIG. 4A, or the bar-graphed difference value resulting from subtraction from a second image scan, as shown in FIGS. 5B, 5D and 5F. Alternatively, the reference image may be "colorized" with a color brightness instead of gray-scale brightness, and can be displayed overlaid upon the second ultrasound image. Alternatively, a small, separate display of the reference ultrasound image overlaid on the second ultrasound image can be displayed beside the second ultrasound image, similar to the graphical indicators mentioned above.

The second ultrasound image is displaced in time (i.e., acquired later) than the reference image, and displayed on the same display as the reference's graphical representation. The second, and any subsequent images, can be referred to as the "live" images, or the real-time images. By displaying the reference image and the live images, a user of the system can determine relative probe position between the two images, and can determine whether scene shift has occurred between the two images. This is useful for determining probe motion, and thus, is useful for detecting a change of relative probe position.

It should be mentioned that the reference ultrasound image may be obtained long before (for example, many weeks or months) the second ultrasound image and can be stored on the ultrasound system 300. The second, and subsequent ultrasound images are typically obtained close together in time. This is so because it may be important for certain ultrasound studies to match the scans from previous visits of the same patient. That is, the latest image sequence (the second and subsequent ultrasound images) may be matched with the reference, or "baseline" images taken previously. Displaying the graphical representation of the reference image allows the sonographer to confirm that he/she is obtaining a clinically comparable image in the current session, without scene shift. Indeed, this example covers the situation where the sonographer raises the probe for a minute before scanning again and also the case where the patient comes back a year or more later.

With reference to the figures, the first ultrasound reference image can be the first ultrasound image 405, and the graphical representation of that image can be the outline 406. The second ultrasound image can be the subsequent ultrasound image 415 in FIG. 4B. The subsequent ultrasound image 415 is shown with the graphical representation (i.e., the outline 406) of the first ultrasound image in FIG. 4B.

Similarly, FIG. 5B shows the subsequent ultrasound image 515 with the graphical representation of the reference image 505 displayed as bar graph 521. In this example, the reference image (i.e., the first ultrasound image 505) is not displayed with the subsequent ultrasound image 515, and is instead stored in the memory 340 (FIG. 3) for use in the image subtraction example, as described above.

Figure 5H:
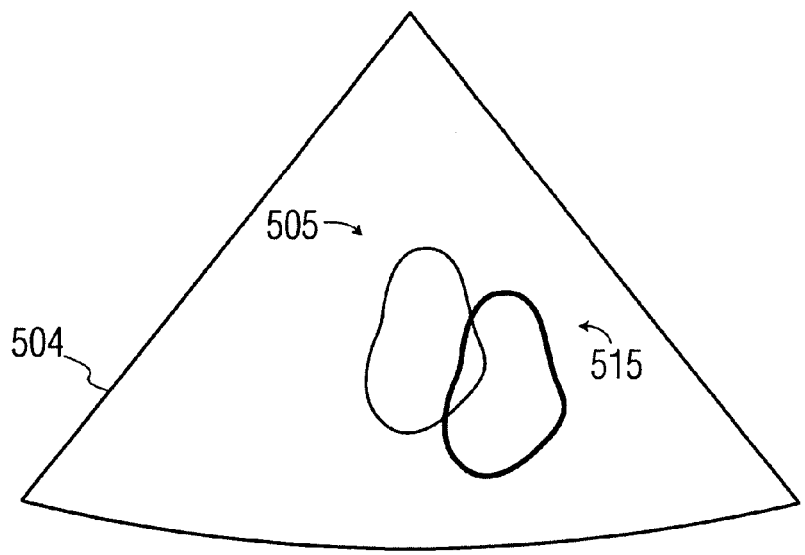

Although omitted for simplicity, the graphical representation of the reference image may have a differentiating color from the second (subsequent) ultrasound image. Such a "colorized" reference image is illustrated in FIG. 5H, in which the second ultrasound image 515 is illustrated using a heavy line and the reference ultrasound image 505 is illustrated using a light line. In practice it would be desirable to have the "colorized" reference image appear bright enough so that it can be distinguished from the subsequent image, but dim enough so that it doesn't interfere with viewing the subsequent image(s) in detail.

Figure 6:
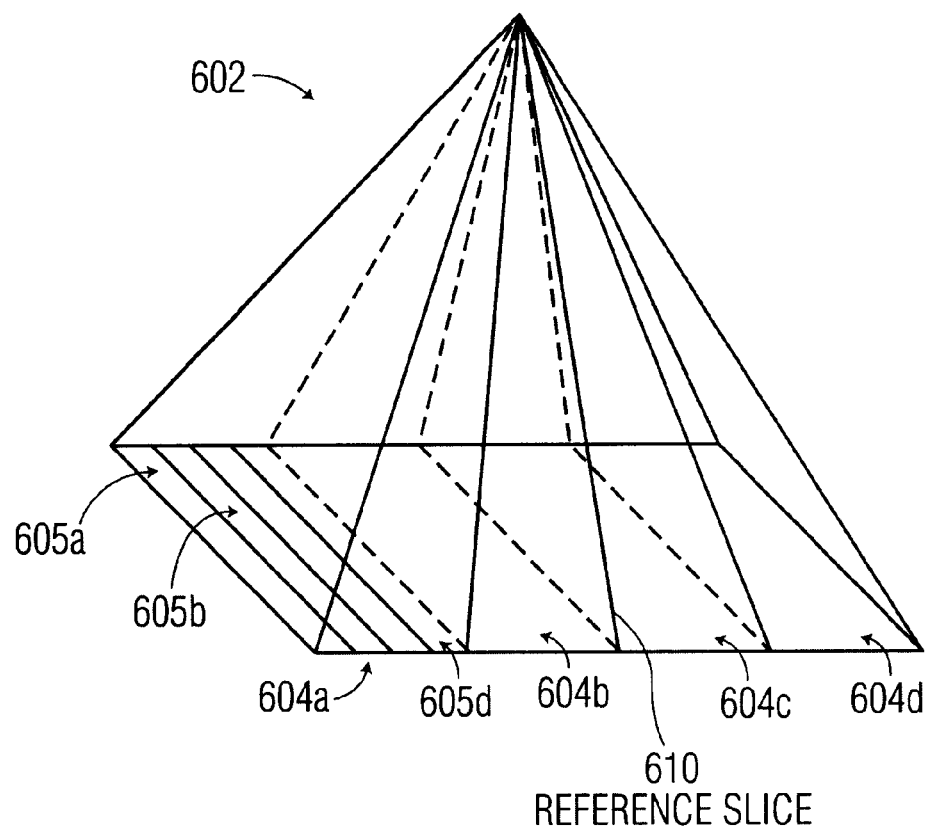
FIG. 6 is a graphical illustration showing another application of the scene shift detection software of FIG. 3.

FIG. 6 is a graphical illustration showing another application in which the scene shift detection software 370 is applicable. FIG. 6 includes a scan volume 602 that is divided into a plurality of sub-volumes 604a, 604b, 604c and 604d. When employing 3D ultrasound imaging to interrogate a volume such as scan volume 602, the frame rate and the frame time, as mentioned above, generally limit the total volume that can be scanned and processed with conventional ultrasound processing equipment. To maximize the ability of the ultrasound imaging system 300 to perform 3D imaging, a scan volume 602 is divided into a number of sub-volumes. Each sub-volume preferably comprises a plurality of parallel slices, each slice separated from the others in one dimension by a regular step. The positions of the separate slices are depicted graphically within sub-volume 604a using reference numerals 605a, 605b, 605c and 605d. The parallel slices 605a, 605b, 605c and 605d intersect with the bottom of the sub-volume 604a. Each sub-volume is scanned separately from the others and multiple times in succession through a pre-determined time period such as a triggered heart cycle, before the next sub-volume is scanned. During the successive sub-volume acquisitions, a single chosen image slice acquired with each sub-volume (but not necessarily located within the sub-volume) is preferably displayed to the user on the display unit 330 (FIG. 3), so that the user can visualize the progress of the full-volume acquisition. After all the sub-volumes have been acquired, each comprising multiple scans over an equivalent length time period, the image data from each is concatenated into the overall volume 602, and is replayed for the user in an image display loop that combines the loops of each sub-volume.

Despite the fact that the sub-volumes were acquired at different times, the correlation of the moving tissues at the different positions gives the user the illusion that all the sub-volumes were acquired during the same time period, and the overall volume is generally useful diagnostically.

Unfortunately, when scanning sub-volumes, scene shift can obscure the results of the sub-volume scans when they are concatenated in this way, and the resulting overall volume can be distorted by mismatches in the position of the moving tissues at the seams between sub-volumes. The system of the invention serves to inform the user that such distortion is happening during the acquisition. In this manner, the user can determine early in the acquisition cycle whether to terminate the acquisition and begin again without having to collect all the data and examine the resulting overall volume display.

A series of sub-volumes can be interrogated, where each sub-volume scan is triggered at a specified delay after, for example, the ECG signal. A sub-volume can be scanned multiple times during a heartbeat, producing a moving image sequence when the sub-volumes (604a–604d) are concatenated. The overall result is a single heartbeat display that may be continuously replayed as a full-size rendered volume. However, as mentioned above, such 3D acquisition over multiple heartbeats is sensitive to scene shift because the relative positions of the rendered sub-volumes must be true to the position of the target that the system assumed when it shifted the beam locations for each successive sub-volume scan. A reference slice 610, which can appear at any location within the scan volume 602, can be used as a reference in determining whether scene shift has occurred. As mentioned above, the system can display a single slice acquired with each sub-volume scan to serve as an indicator of scan acquisition progress during the acquisition itself, before concatenation and display of the overall volume. A reference slice can be scanned with each sub-volume. Such a reference slice is illustrated for volume 602 for example using reference numeral 610 and shows a constant image position during acquisition of each sub-volume, and thus can be used to detect scene shift between sub-volumes. By employing any of the border formation software 375 or the image subtraction software 380 or reference slice 610, in combination with the scene shift detection software 370, it is possible to determine whether scene shift has occurred from one sub-volume to subsequent sub-volumes, thereby allowing a user of the ultrasound imaging system 300 to determine whether an additional ultrasound procedure be performed.

Figure 7:
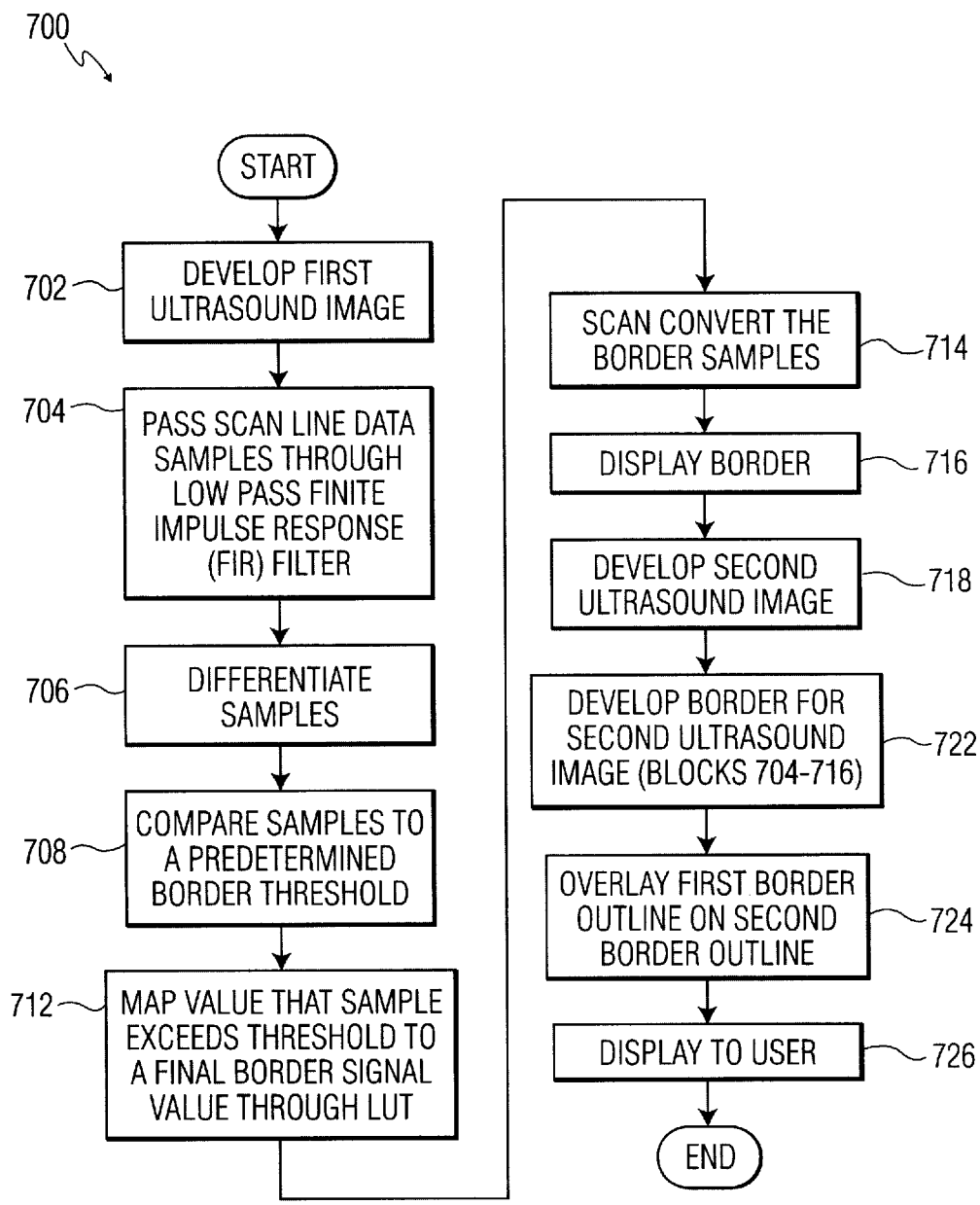
FIG. 7 is a flow chart describing the operation of the border formation software of FIG. 3.

FIG. 7 is a flow chart 700 describing the operation of the border formation software 375 of FIG. 3. In block 702 a first ultrasound image is developed. The border of the first ultrasound image is developed as follows. In block 704, acoustic samples from data used to generate the first ultrasound image are passed through a low-pass FIR filter. In block 706, the samples are differentiated using the nth difference (the numerical difference between the current sample and the nth previous sample). In block 708, output samples of the difference step 706 are each compared to a pre-determined threshold, which may be adjusted by the user to control the sensitivity of the border detection.

In block 712, the numerical amount, or value, by which the sample exceeds the border threshold is mapped to a final border signal value through the look-up table (LUT) 385 located in the memory 340. In block 714, the border signal samples are scan converted in the scan converter 328 and displayed like the image data, preferably overlaying the border in a different display color. In block 716, the border outline is displayed to a user of the system.

In block 718 a second (subsequent) ultrasound image is developed. In block 722, a border outline of the second ultrasound image is generated as described in blocks 704 through 716. In block 724, the border outline of the first ultrasound image is overlaid over the border outline of the second ultrasound image developed in block 718. In block 726 the first border outline overlaid over the second border outline is displayed (via display unit 330) to a user of the ultrasound system 300. In this manner, a user of the ultrasound system 300 can immediately determine whether scene shift has occurred over multiple ultrasound frames and can determine whether another ultrasound scan should be performed.

Figure 8:
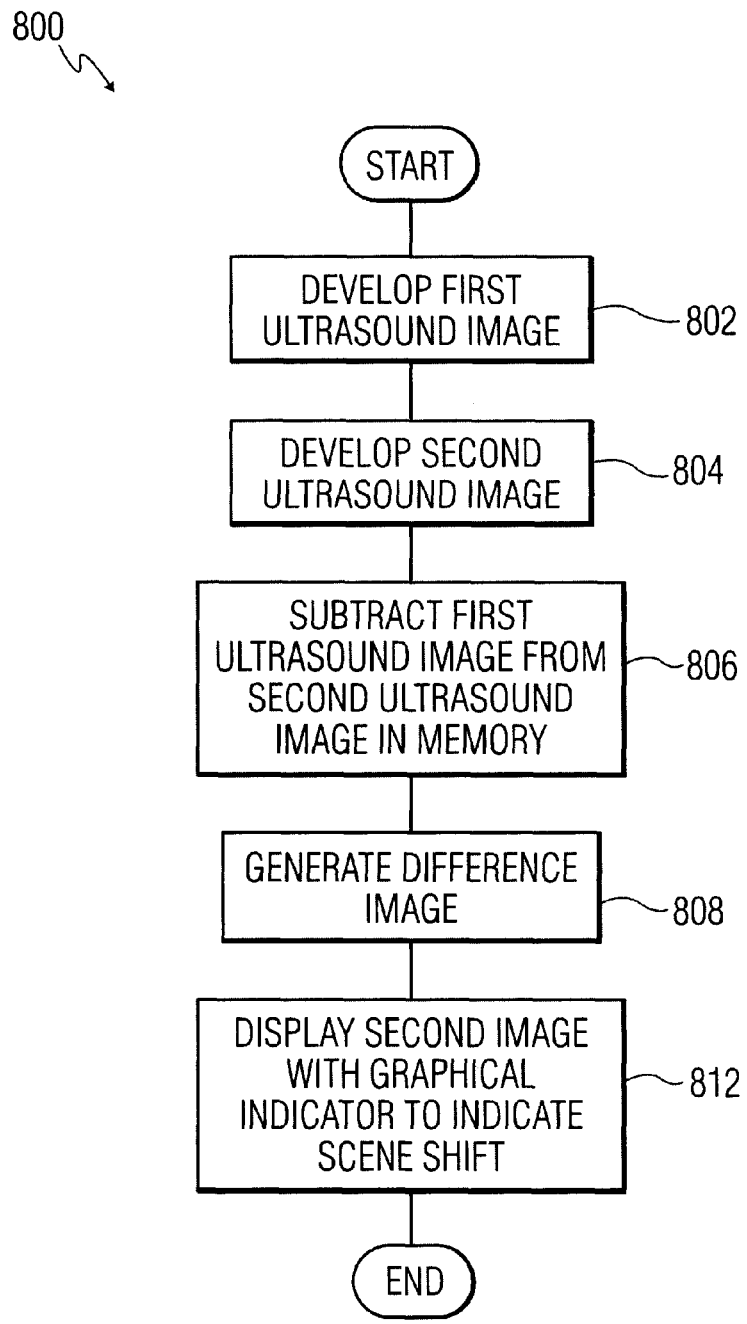
FIG. 8 is a flow chart describing the operation of the image subtraction software of FIG. 3.

FIG. 8 is a flow chart 800 describing the operation of the image subtraction software 380. In block 802 a first ultrasound image is collected and developed. In block 804 a second ultrasound image is collected and developed.

In block 806 the image subtraction software 380 subtracts the first ultrasound image from the second ultrasound image in memory 340. In block 808 a difference image is developed and, in block 812, a graphic indicator of relative scene shift between the first and second ultrasound images is displayed to a user via the display unit 330 (FIG. 1). In this manner, a user of the ultrasound imaging system 300 can determine whether scene shift has occurred during multiple image frames.

It will be apparent to those skilled in the art that many modifications and variations may be made to the present invention, as set forth above, without departing substantially from the principles of the present invention. For example, the present invention can be used with any ultrasound imaging system. Instead of a matrix probe, an ultrasound probe that employs a 1-D element array may be mechanically oscillated automatically, or swept back and forth manually to create a sets of 3D images for which scene shift can be detected as described previously. Instead of a matrix array, a 1-D probe may be used to develop 2D images that again require detection of scene shift, such as for myocardial perfusion measurement. Furthermore, another method for generating highlighted images to determine whether scene shift has occurred is to process the first ultrasound image data and the second ultrasound image data using low-gray-scale compression, effectively suppressing dim structures and emphasizing bright ones. In a manner similar to developing border information, this produces a reduction of the image that can be overlaid on an original ultrasound image, in a differentiating color. A superimposed sequence of highlight images will reveal relative translation of the bright structures, since they will appear smeared if there has been motion of the image during the scan sequence. Furthermore, the invention is applicable to various ultrasound imaging systems and components. All such modifications and variations are intended to be included herein.

What is claimed is:

1. A system for real-time visualization of scene shift of an object in an ultrasound scan, comprising:

means for developing a first ultrasound image;
means for determining a first border of the object in the first ultrasound image;
means for developing a second ultrasound image;
means for determining a second border of the object in the second ultrasound image;
means for forming an overlay of the first border on the second border; and
display means for simultaneously displaying only the second border and the overlay of the first border on the second border to a user without displaying the entire object to enable the user to determine whether the first border aligns with the second border.

2. The system of claim 1, wherein the means for forming the overlay comprises means for directing the display means to highlight the first border in a color different from a color of the second border.

3. The system of claim 1, further comprising:
means for capturing a plurality of ultrasound images corresponding to a time cycle;
means for developing a corresponding plurality of reference images; and
means for forming an overlay of one of the plurality of reference images over a subsequent image, where the reference image is selected based upon a trigger event,
the display means being arranged to display the subsequent image and the overlay of the one of the plurality of reference images over the subsequent image.

4. The system of claim 1, wherein the display means are arranged to display the object in the second ultrasound image in a different color than a color in which the second border is displayed.

5. The system of claim 1, wherein the display means are arranged to display the first border differently than the second border.

6. A system for real-time visualization of scene shift in an ultrasound scan, comprising:
first developing means for developing a first ultrasound image;
second developing means for developing a plurality of additional ultrasound images after the first ultrasound image is developed;
subtracting means for subtracting the first ultrasound image from a first one of the plurality of additional ultrasound images to generate a first difference image and for subtracting each of the plurality of additional ultrasound images from an immediately following developed one of the plurality of additional ultrasound images to generate additional difference images;
indicator means for sequentially displaying the first and additional difference images to enable a user to determine whether the first ultrasound image aligns with the first one of the plurality of additional ultrasound images and whether each of the plurality of additional ultrasound images aligns with the immediately following one of the plurality of additional ultrasound images.

7. The system of claim 6, wherein the indicator means comprises means for indicating portions of the first ultrasound image that are misaligned with respect to the first one of the plurality of additional ultrasound images.

8. The system of claim 6, wherein the indicator means are arranged to display a relative misalignment between the first ultrasound image and the first one of the plurality of additional ultrasound images to the user.

9. A method for real-rime visualization of scene shift of an object in an ultrasound scan, comprising:
developing a first ultrasound image;
determining a first border of the object in the first ultrasound image;
developing a second ultrasound image;
determining a second border of the object in she second ultrasound image;
forming an overlay of the first border on the second border; and
simultaneously displaying only the second border and the overlay of the first border on the second border to a user without displaying the entire object to enable the user to determine whether the first border aligns with the second border.

10. The method of claim 9, wherein the displaying step comprises highlighting the first border in a color different from a color of the second border.

11. The method of claim 9, wherein the displaying step comprises the step of displaying the object in the second ultrasound image in a different color than a color in which the second border is displayed.

12. The method of claim 9, wherein the displaying step comprises the step of displaying the first border differently than the second border.

13. The method of claim 9, further comprising:
developing at least one additional ultrasound image;
determining a border of the object in each of the at least one additional ultrasound image;
forming an overlay of the first border, the second border and any preceding determined borders on the border of the object in each of the at least one additional ultrasound image; and
simultaneously displaying the border of the object in each of the at least one additional ultrasound image and the overlay of the first border, the second border and any preceding determined borders on the border of the object in each of the at least one additional ultrasound image.

14. A method for real-time visualization of scene shift in an ultrasound scan, comprising:
developing a first ultrasound image;
developing a plurality of additional ultrasound images after the first ultrasound image is developed;
subtracting the first ultrasound image from a first one of the plurality of additional ultrasound images to generate a first difference image;
displaying the first difference image to enable a user to determine whether the first ultrasound image aligns with the first one of the plurality of additional ultrasound images;
subtracting each of the plurality of additional ultrasound images from an immediately following developed one of the plurality of additional ultrasound images to generate additional difference images; and
sequentially displaying the additional difference images to enable a user to determine whether each of the plurality of additional ultrasound images aligns with the immediately following one of rho plurality of additional ultrasound images.

15. The method of claim 14, wherein she displaying step comprises indicating portions of the first ultrasound image that are misaligned with respect to the first one of the plurality of additional ultrasound images.

16. The method of claim 14, wherein the displaying step comprises indicating a relative misalignment between the first ultrasound image and the first one of the plurality of additional ultrasound images to the user.

17. A system for real-rime visualization of scene shift of an object in an ultrasound scan, comprising:
- an ultrasound receiver for developing a first ultrasound image and a second ultrasound image;
- border formation software coupled to rho ultrasound receiver for determining a first border of the object in the first ultrasound image and a second border of the object in the second ultrasound image;
- image misalignment detection software coupled to the border formation software for forming an overlay of the first border on the second border; and
- a display coupled to the border formation software and the inane misalignment software for simultaneously displaying only the second border and the overlay of the first order on the second border to a user without displaying the entire object to enable the user to determine whether the first border aligns with the second border.

18. The system of claim 17, wherein the image misalignment detection software is arranged to direct the display to highlight the first border in a color different from a color of the second border.

19. The system of claim 17, wherein the ultrasound receiver captures a plurality of ultrasound images corresponding to a time cycle and develops a corresponding plurality of reference images, and overlays one of the plurality of reference images ever a subsequent image, where the reference image is selected based upon a trigger event, the display being arranged to display the subsequent image and the overlay of the one of the plurality of reference images ever the subsequent image.

20. The system of claim 17; wherein the display is arranged to display the object in the second ultrasound image in a different color than a color in which the second border is displayed.

21. The system of claim 17, wherein the display is arranged to display the first border differently than the second border.

22. A computer-readable medium having a program for real-time visualization of scene shift of an object in an ultrasound scan, the program comprising logic for:
- developing a first ultrasound image;
- determining first border of the object in the first ultrasound image;
- developing a second ultrasound image;
- determining a second border of the object in the second ultrasound image;
- forming an overlay of the first border on one second border; and
- simultaneously displaying only the second border and the overlay of the first border on the second border to a user without displaying the entire object to enable the user to determine whether the first border aligns with The second border.

23. The program of claim 22, wherein the displaying step comprises highlighting the first border in a color different from a color of the second border.

24. A computer-readable medium having a program for real-time visualization of scene shift in an ultrasound scan, the program comprising logic for:
- developing a first ultrasound image;
- developing a plurality of additional ultrasound images after the first ultrasound image is developed;
- subtracting the first ultrasound image from a first one of the plurality of additional ultrasound images to generate a first difference image;
- displaying the first difference image to enable a user to determine whether the first ultrasound image aligns with the first one of the plurality of additional ultrasound images;
- subtracting each of the plurality of additional ultrasound images from an immediately following developed one of the plurality of additional ultrasound images to generate additional difference images; and
- sequentially displaying the additional difference images to enable a user to determine whether each of the plurality of additional ultrasound images aligns with the immediately following one of the plurality of additional ultrasound images.

25. The program of claim 24, further comprising logic for indicating portions of the first ultrasound image that are misaligned with respect to the first one of the plurality of additional ultrasound images.

26. The program of claim 24, further comprising logic for indicating a relative misalignment between the first ultrasound image and the first one of the plurality of additional ultrasound images to the user.

27. A system for real-time visualization of relative probe position in an ultrasound scan sequence, comprising:
- means for developing a first ultrasound reference image;
- means for developing a graphical representation of the reference image for display;
- means for developing a second ultrasound image;
- means for forming an overlay of the graphical representation of the reference image on the second ultrasound image; and
- display means for simultaneously displaying only the second ultrasound image and the overlay of the graphical representation of the reference image on the second ultrasound image without displaying the entire reference image.

28. The system of claim 27, wherein the display means are arranged to display the reference image in color different than a color of the second ultrasound image.

29. The system of claim 27, wherein the graphical representation of the reference image is stored on the system for use as reference for a second of ultrasound scan acquired in a separate scan sequence from the one use to acquire the reference image.

30. A method for real-time visualization of relative probe position in an ultrasound scan sequence, comprising:
- developing a first ultrasound reference image;
- developing a graphical representation of the reference image for display;
- developing a second ultrasound image;
- forming an overlay of the graphical representation of the reference image on the second ultrasound image; and
- simultaneously displaying only the second ultrasound image and the overlay of the graphical representation of the reference image on toe second ultrasound image without displaying the entire reference image.

31. The method of claim 30, wherein the displaying step comprises displaying the reference image in a color different than a color of the second ultrasound image.

32. The method of claim 30, further comprising storing the graphical representation of the reference image on the system for use as a reference for a second ultrasound scan acquired in a separate scan sequence from the one used to acquire rho reference image.

33. A system for real-time visualization of scene shift of an object in an ultrasound scan, comprising:
- mean for developing a first ultrasound image;
- mean for determining a first border of the object in the first ultrasound image;
- means for developing a second ultrasound image;
- means for determining a second border of the object in the second ultrasound image;
- means for forming an overlay of the first border on the second border;
- means for capturing a plurality of ultrasound images corresponding to a time cycle;
- means for developing a corresponding plurality of reference images;
- means for forming an overlay of one of the plurality of reference images over a subsequent image, where the reference image is selected based upon a trigger event; and
- display means for simultaneously displaying the second border and the overlay of the first border on the scored border to a user to enable the user to determine whether the first border aligns with the second border, the display means being arranged to display the subsequent image and the overlay of the one at the plurality of reference images over the subsequent image.

* * * * *